(12) United States Patent
Goto et al.

(10) Patent No.: US 6,242,654 B1
(45) Date of Patent: Jun. 5, 2001

(54) PREPARATION PROCESS OF FLUORINE SUBSTITUTED AROMATIC COMPOUND

(75) Inventors: Kenichi Goto; Kouki Fukumura; Hiroshi Sonoda; Junko Naruse; Hidetoshi Hayashi; Hideaki Oikawa, all of Fukuoka-ken (JP)

(73) Assignee: Mitsui Chemicals, Inc. (JP)

( * ) Notice: Subject to any disclaimer, the term of this patent is extended or adjusted under 35 U.S.C. 154(b) by 0 days.

(21) Appl. No.: 09/469,165

(22) Filed: Dec. 21, 1999

(30) Foreign Application Priority Data

Dec. 22, 1998 (JP) .................................................. 10-364163
Sep. 29, 1999 (JP) .................................................. 11-275524
Oct. 8, 1999 (JP) .................................................. 11-287989

(51) Int. Cl.$^7$ .......................... C07C 43/257; C07C 19/08
(52) U.S. Cl. .......................... 568/655; 568/936; 558/303; 570/127
(58) Field of Search ..................... 570/123, 124, 570/127; 568/630, 631, 649, 655, 927, 928, 936; 558/303

(56) References Cited

U.S. PATENT DOCUMENTS 3,914,265    10/1975    Middleton .
3,976,691    8/1976    Middleton .

FOREIGN PATENT DOCUMENTS

0895991A2    2/1999    (EP) .
11 181022A    7/1999    (JP) .

OTHER PUBLICATIONS

CAREACT: 116:128265 abs of Org Prep Proced Int 24(1) pp 55–7 by Dust et al, 1992.*

* cited by examiner

Primary Examiner—Jean F. Vollano
(74) Attorney, Agent, or Firm—Burns, Doane, Swecker, & Mathis, L.L.P.

(57) ABSTRACT

A preparation process of a fluorine substituted aromatic compound comprising reacting an alkali metal or alkali earth metal salt of an aromatic compound having a hydroxy group with an organic fluorinating agent is disclosed. As a representative fluorinating agent, a bis-dialkylamino-difluoromethane compound, for example, 2,2'-difluoro-1,3-dimethylimidazolidine, is exemplified. According to the process, an industrially useful fluorinated aromatic compound, for example, a fluorobenzene, a fluorine substituted benzophenone, a fluorine substituted diarylsulfone can be prepared with ease in economy without specific equipment.

2 Claims, No Drawings

PREPARATION PROCESS OF FLUORINE SUBSTITUTED AROMATIC COMPOUND

BACKGROUND OF THE INVENTION

1. Field of the Invention

The present invention relates to a preparation process of fluorine substituted aromatic compounds, and more specifically, relates to a process for preparing substituted fluorobenzene, fluorine substituted benzophenone and fluorine substituted diaryl sulfone by fluorinating an alkali metal or alkali earth metal salt of corresponding hydroxy aromatic compounds.

2. Prior Art of the Invention

Fluorine substituted aromatic compounds have specific characteristics due to fluorine and some compounds are useful in industry.

For example, substituted fluorobenzene is applied to a raw material or intermediate of physiologically active substances or functional materials for use in medicines and agriculture chemicals, and is also utilized in a wide field such as refrigerant, resin material and lubricant. Fluorine substituted benzophenone is also generally used for a raw material of polyether polyketone including polyether ether ketone which is a superengineering plastic having excellent thermal resistance, electrical insulation, sliding property and chemical resistance.

Fluorine substituted benzophenone is also used for flame retardant, painkiller, platelet aggregation inhibitor, thrombosis inhibitor and other functional chemicals or an intermediate of these functional chemicals and thus is also useful in the field of medicines and agricultural chemicals.

Further, fluorine substituted diaryl sulfone is commonly used for a raw material of polysulfone including polyether sulfone which is an engineering plastic having excellent thermal resistance, electrical insulation, sliding property and chemical resistance, and is also used for a raw material of functional materials such as an organic EL material and an intermediate of medicines and agricultural chemicals such as an anti-cancer drug and immune deficiency suppressor and thus is a required compound in industry.

The preparation process of these compounds has conventionally been investigated and following processes have been known.

The preparation process of substituted fluorobenzene can be divided into two main classes, that is, a process for preparing the desired compound by carrying out the reaction using fluorobenzene which already contains a fluorine atom, and a process for preparing the desired compound by the fluorine substituting reaction of benzene compounds having various functional groups.

The former process often uses expensive raw materials. On the other hand, the latter process can prepare the desired, substituted fluorobenzene by using cheap raw materials and thus fluorinating reaction technology which enables the desired substituted reaction has been demanded.

The following processes have been known for preparing fluorine substituted benzophenone.

EP 69598, EP 178184, EP 147299 and Japan Laid Open SHO 61-221146 have disclosed a Friedel-Crafts reaction using fluorobenzene and p-fluoro-benzoyl chloride.

Japanese Laid Open Patent SHO 58-126829 has disclosed a preparation process from 1,1-bis(4-fluorophenyl)-2,2-dichloroethylene, Japanese Laid-Open Patent SHO 57-154139 has disclosed a process from 1,1-bis(4-fluorophenyl)-2,2-trichloroethanol, and AU 533574 and Japanese Laid Open Patent SHO 57-169441 have disclosed a process from 4,4'-dichlorobenzophenone.

These preparation processes use raw materials containing fluorine or other halogen atoms, and thus much labor is required in the raw material preparation step.

As to a process for substituting fluorine for a functional group on an aromatic ring, the Balz-Schiemann reaction which replaces an amino group has been known and also utilized for preparing fluorine substituted benzophenone as desired in Japanese Laid-Open Patent SHO 54-132558. In the process, a large excess of hydrogen fluoride has been used for replacing the amino group with fluorine.

Further, conventionally known processes for preparing fluorine substituted diaryl sulfone from fluorobenzene and other fluoro aromatic compounds as a starting material are a process for reacting with chloro-sulfonic acid or fluoro-sulfonic acid as described in J. Am Chem. Soc., 62, 5111940, Japanese Laid Open Patent SHO 58-206552 and HEI 1-250342; a process for reacting with concentrated sulfuric acid in the presence of boron trifluoride and hydrogen fluoride as described in EP 147298; and a process for reacting with aryl-sulfonyl chloride as described in J. Am. Chem. Soc., 70, 654(1948) and J, Japan Chem. Soc., 76, 775–8(1955).

Other processes by using oxidation reaction of 4,4'-difluorodiphenyl sulfide and 4,4'-difluorodiphenyl sulfoxide have been described in J. Am. Chem. Soc., 70, 1564 (1948) and Acta, Chim. hug., 4, 111(1954). Any of these processes uses expensive fluoro-aromatic compounds as a raw material and is thus disadvantageous in industry.

On the other hand, fluorinating agents which have been used for a fluorination reaction include fluorine, hydrogen fluoride, sulfur tetra-fluoride and diethylaminosulfur trifluoride.

However, these conventional fluorinating agents are difficult to handle because of toxicity, corrosive property, and danger of explosion during the reaction time and thus specific equipment and technique have been required. For example, representative fluorinating agents which are effective for a direct conversion reaction from a hydroxyl group to a fluorine group include sulfur tetrafluoride ($SF_4$) and diethylaminosulfur trifluoride (DAST).

However, $SF_4$ has high toxicity and difficulty in handling causes problems.

On the other hand, DAST has been known as an useful fluorinating agent which can efficiently fluorinate a hydroxyl, ketone, carboxyl and other oxygen containing groups under mild conditions as described in U.S. Pat. No. 3,976,691. However, DAST is prepared by reacting highly dangerous $SF_4$ with dimethylaminotrimethyl silane at a low temperature from −78° C. to −60° C, and thus specific reaction equipment is required.

As to safety, explosion in the preparation and use of DAST has been reported in J. Fluorine Chem., 42, 137 (1989).

As mentioned above, fluorine gas, hydrogen fluoride and sulfur tetrafluorine gas have been conventionally used as a fluorinating agent for preparing a fluorine compound.

These fluorinating agents have led to problems upon difficulty in handling due to toxicity, corrosive property, danger of explosion during the reaction time, and requirement for specific equipment and technique. In recent years, various fluorinating agents have been developed in order to overcome these problems.

However, the development of a fluorinating agent, which can be used in industry, has been still unsatisfactory in view of a preparation process, selectivity in the reaction, yield and economy.

Thus, a safe, steady and economical preparation process of fluorine substituted benzophenone by using a fluorinating agent has not yet been found.

Another process for reacting diaryl-sulfone which has halogen other than fluorine or a nitro group as a substituent with KF at a high temperature above 200° C. in an aprotic polar solvent in the presence of a specific ammonium salt or an organometal complex has been described in WO 8704148–8704150 and Japanese Laid Open Patent HEI 2-273626.

However, these processes are difficult in reaction conditions and thus unfavorable in industry. A process for reacting 4,4'-dinitrodiphenyl sulfone with tetramethylammonium fluoride under relatively mild condition in an aprotic polar solvent has been reported in J. Fluorine Chem., 70(2), 201(1995). However, pure tetramethylammonium fluoride is difficult to prepare and thus is an expensive fluorinating agent. Consequently, the process is also disadvantageous in industry.

Under these circumstances, it has been strongly desired for fluorine substituted diaryl sulfone to develop an economical and readily realizable preparation process in industry.

SUMMARY OF THE INVENTION

One object of the invention is to provide an economical preparation process of fluorine substituted aromatic compound in industry.

Another object of the invention is to provide a process for efficiently preparing substituted fluorobenzene, fluorine substituted benzophenone, fluorine substituted diaryl sulfone and other useful fluorine substituted aromatic compounds from hydroxybenzene, hydroxybenzophenone, hydroxydiaryl sulfone and other hydroxyaromatic compounds.

As a result of an intensive investigation in order to achieve these objects, the present inventors have found that the reaction yield can be improved by reacting an alkali metal or alkali earth metal salt of hydroxyaromatic compound with a fluorinating agent and that fluorine substituted aromatic compounds which are useful in industry, particularly, substituted fluorobenzene, fluorine substituted benzophenone and fluorine substituted diaryl sulfone can be economically prepared in industry by using the process. Thus, the present invention has been completed.

In the preparation process, the inventors have found in particular a bis-dialkylamino difluoromethane compound represented by the formula (5);

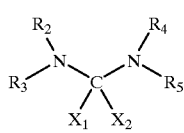

(5)

wherein $R_2$, $R_3$, $R_4$ and $R_5$ are an alkyl or aryl group having 1 to 6 carbon atoms, and can be the same or different, $R_2$ and $R_3$ or $R_4$ and $R_5$ can bond to form a ring having a nitrogen atom or a nitrogen atom and other hetero atom. $R_2$ and $R_4$ can bond to form a ring having a nitrogen atom or a nitrogen atom and other hetero atoms, and $X_1$ is a fluorine atom, $X_2$ is a fluorine or chlorine atom, and $X_1$ and $X_2$ can form a covalent bond respectively with a carbon atom or $X_1$ alone can form a covalent bond and $X_2$ can exist in the form of an ion pair, and that the compound is excellent as a novel fluorinating agent of a hydroxyaromatic compound, that from preparation to use in fluorination of the compound can be carried out in high safety and with ease without requiring specific equipment or technique, and that, after finishing the fluorination reaction the compound can be recovered in the form of tetra-alkyl urea which is a starting material, regenerated to provide a fluorinating agent and economically reused.

That is, one aspect of the invention is;

1. A preparation process comprising reacting a compound represented by formula (1)

(1)

wherein M is an alkali metal or alkali earth metal atom, a and b are an integer of 1 to 5 and can be the same or different and a+b is 6 or less, and $X_1$ is a mono-valent group selected from the groups consisting of the following (a), (b) and (c).

(a) a mono-valent group selected from the groups consisting of a halogen atom, an alkyl, alkoxy, aryl, aryloxy, nitro, cyano, acyl, per-halogenated alkyl, per-halogenated alkoxy, alkylsulfonyl, arylsulfonyl, alkylsulfoxide, arylsulfoxide, alkylsulfide and arylsulfide group.

(b) a group represented by the formula (2);

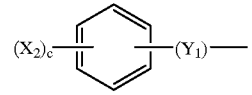

(2)

wherein $Y_1$ is a divalent group selected from a sulfonyl, sulfoxide, sulfide, ether, carbonyl, alkylene group having 1 to 3 carbon atoms, perfluoroalkylene group having 1 to 3 carbon atoms and direct bond, and $X_2$ is a monovalent group selected from the group consisting of a monovalent group shown by the above $X_1$ and an alkali metal or alkali earth metal salt of a hydroxyl group, and c is an integer of 1 to 5, and (c) a group represented by the formula (3);

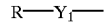

(3)

wherein $Y_1$ is the same as the formula (2) and R is a perhalogenated alkyl group; with an organic fluorinating agent to prepare a fluorine substituted aromatic compound represented by the formula (4);

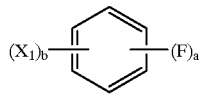
(4)

wherein a, b and $X_1$ are the same as the above formula (1).

2. A preparation process according to the above 1 wherein the compound represented by the formula (1) is phenolate represented by the formula (1-1);

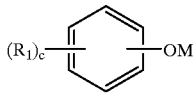
(1-1)

wherein M is an alkali metal or alkali earth metal atom, c is an integer of 1 to 5, and $R_1$ is a halogen atom, an alkyl, alkoxy, aryl, aryloxy, nitro, cyano, acyl, perhalogenated alkyl, perhalogenated alkoxy, alkylsulfonyl, arylsulfonyl, alkylsulfoxide, arylsulfoxide, alkylsulfide or arylsulfide group.

3. A preparation process according to the above 1 wherein the fluorine substituted aromatic compound represented by the formula (4) is substituted fluorobenzene represented by the formula (4-1);

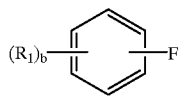
(4-1)

wherein b is an integer of 1 to 5 and $R_1$ is a halogen atom, an alkyl, alkoxy, aryl, aryloxy, nitro, cyano, acyl, perhalogenated alkyl, perhalogenated alkoxy, alkylsulfonyl, arylsulfonyl, alkylsulfoxide, arylsulfoxide, alkylsulfide or arylsulfide group.

4. A preparation process according to the above 1 wherein the compound represented by the formula (1) is an alkali metal or alkali earth metal salt of hydroxy-benzophenone represented by the formula (1-2);

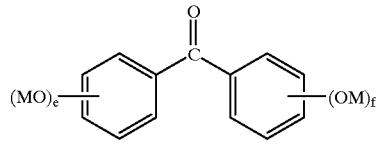
(1-2)

wherein e and f are an integer of 0 to 5, and can be the same or different, however, f is 1 or more when e is 0 and e is 1 or more when f is 0, and M is an alkali metal or alkali earth metal atom.

5. A preparation process according to the above 1 wherein the fluorine substituted aromatic compound represented by the formula (4) is fluorine substituted benzophenone represented by the formula (4-2);

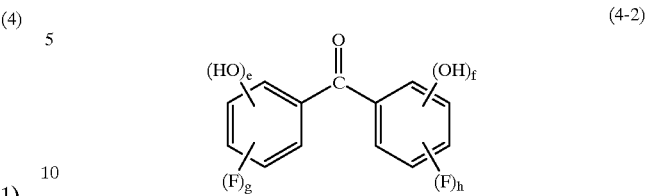
(4-2)

wherein g and h are 0 or 1 and not simultaneously 0, and e and f are 0 or 1 and not simultaneously 1, and e is 0 or 1 when g is 0, e is 0 when g is 1, f is 0 or 1 when h is 0, and f is 0 when h is 1.

6. A preparation process according to the above 5 wherein the compound represented by the formula (1) is 4,4'-dihydroxybenzophenone and the fluorine substituted aromatic compound represented by the formula (4) is 4,4'-difluorobenzophenone.

7. A preparation process according to the above 5 wherein the compound represented by the formula (1) is 4,4'-dihydroxybenzophenone and the fluorine substituted aromatic compound represented by the formula (4) is 4-hydroxy-4'-fluorobenzophenone.

8. A preparation process according to the above 1 wherein the compound represented by the formula (1) is an alkali metal or alkali earth metal salt of dihydroxydiaryl sulfone represented by the formula (1-3);

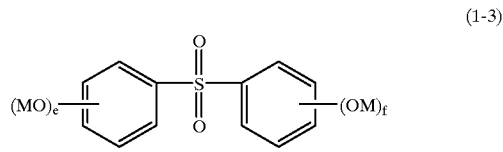
(1-3)

wherein e, f and M are the same as the formula (1-2).

9. A preparation process according to the above 1 wherein the fluorine substituted aromatic compound represented by the formula (4) is fluorine substituted diaryl sulfone represented by the formula (4-3);

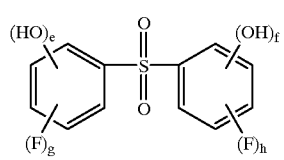
(4-3)

wherein g and h are 0 or 1 and not simultaneously 0, e and f are 0 or 1 and not simultaneously 1, e is 0 or 1 when g is 0 and e is 0 when g is 1, and f is 0 or 1 when h is 0 and f is 0 when h is 1.

10. A preparation process according to the above 9 wherein the compound represented by the formula (1) is 4,4'-dihydroxybiphenylsulfone and the fluorine substituted aromatic compound represented by the formula (4) is 4,4'-difluorodiphenyl sulfone.

11. A preparation process according to the above 9 wherein the compound represented by the formula (1) is 4,4'-dihydroxydiphenylsulfone and the fluorine substituted aromatic compound represented by the formula (4) is 4-hyroxy-4'-fluorodiphenyl sulfone.

12. A preparation process according to the above 1 wherein the organic fluorinating agent is a compound represented by the formula (5);

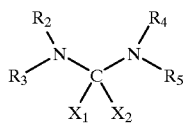

(5)

wherein $R_2$, $R_3$, $R_4$ and $R_5$ are an alkyl or aryl group having 1 to 6 carbon atoms and can be the same or different, $R_2$ and $R_3$ or $R_4$ and $R_5$ can bond to form a ring having a nitrogen atom or a nitrogen atom and other hetero atom, $R_2$ and $R_4$ can bond to form a ring having a nitrogen atom or a nitrogen atom and other hetero atoms, and $X_1$ is a fluorine atom, $X_2$ is a fluorine or chlorine atom, and $X_1$ and $X_2$ can form a covalent bond respectively with a carbon atom or $X_1$ alone can form a covalent bond and $X_2$ can exist in the form of an ion pair.

13. A preparation process according to the above 1 wherein the organic fluorinating agent is a compound represented by the formula (5-1);

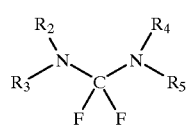

(5-1)

wherein $R_2$, $R_3$, $R_4$ and $R_5$ are the same as the formula (5).

14. A preparation process according to one of the above 1 to 11 wherein the organic fluorinating agent is 2,2'-difluoro-1,3-dimethylimidazolidine represented by the formula (5-2);

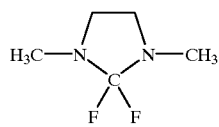

(5-2)

The invention provides a process for safely, steadily and economically preparing the fluorine substituted aromatic compound in industry from an alkali metal or alkali earth metal salt of hydroxy aromatic compound by using the fluorinating agent.

Particularly, by using a bis-dialkylamino-difluoromethane compound as a fluorinating agent, fluorine substituted aromatic compounds such as substituted fluorobenzene, fluorine substituted benzophenone and fluorine substituted diaryl sulfone can be prepared with ease in economy without requiring specific equipment.

PREFERRED EMBODIMENT OF THE INVENTION

The alkali metal or alkali earth metal salt of hydroxyaromatic compound which is used in the invention is an alkali metal or alkali earth metal salt of hydroxyaromatic compound represented by the formula (1);

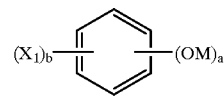

(1)

In the formula (1), M is an alkali metal or alkali earth metal atom, a and b are an integer of 1 to 5 and can be the same or different, and the sum of a and b is 6or less.

$X_1$ is a monovalent group selected from the group consisting of the following (a), (b) and (c):
(a) a mono-valent group selected from the groups consisting of a halogen atom, an alkyl, alkoxy, aryl, aryloxy, nitro, cyano, acyl, perhalogenated alkyl, perhalogenated alkoxy, alkylsulfonyl, arylsulfonyl, alkylsulfoxide, aryl sulfoxide, alkyl sulfide and aryl sulfide group,
(b) a monovalent group represented by the formula (2);

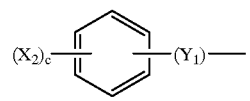

(2)

wherein $Y_1$ is a divalent group selected from a sulfonyl, sulfoxide, sulfide, ether carbonyl, alkylene group having 1 to 3 carbon atoms, perfluoroalkylene group having 1 to 3 carbon atoms and direct bond, and $X_2$ is a mono-valent group selected from the group consisting of a monovalent group shown by the above $X_1$ and an alkali metal or alkali earth metal salt of a hydroxyl group, and c is an integer of 1 to 5, and
(c) a monovalent group selected from the group represented by the formula (3 );

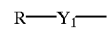

(3)

wherein $Y_1$ is the same as the formula (2) and R is a perhalogenated alkyl group.

In the above (a), any of the arylsulfonyl, arylsulfoxide and arylsulfide group has no substituent.

M in the formula (1) is an alkali metal or alkali earth metal atom, for example, a sodium, potassium, lithium and calcium atom, preferably a sodium and potassium atom.

These salts can be prepared with ease by salt formation and dehydration of the corresponding hydroxy compound by use of, for example, sodium hydroxide or potassium hydroxide.

The aromatic compound corresponding to the alkali metal or alkali earth metal salt of hydroxy aromatic compound represented by the formula (1) includes specifically the following compounds.

(A) $X_1$ is a substituted of group (a) in the formula (1):
2-methylphenol, 3-methylphenol, 4-methylphenol, 2-ethylphenol,
3-ethylphenol, 4-ethylphenol, 2,3-dimethylphenol, 2,4-dimethylphenol,
2,5-dimethylphenol, 2,6-dimethylphenol, 3,4-dimethylphenol,
3,5-dimethylphenol, 2-methoxyphenol, 3-methoxyphenol, 4-methoxyphenol, 2-ethoxyphenol, 3-ethoxyphenol, 4-ethoxyphenol, 2,3-dimethoxyphenol,
2,6-dimethoxyphenol, 3,4-dimethoxyphenol, 3,5-dimethoxyphenol,
2-hydroxybiphenyl, 3-hydroxybiphenyl, 4-hydroxybiphenyl,
2.6-diphenylphenol, 4-phenoxyphenol, 2-nitrophenol, 3-nitrophenol,
4-nitrophenol, 2,4-dinitrophenol, 2,5-dinitrophenol, 2,4,6-trinitrophenol,
2-cyanophenol, 3-cyanophenol, 4-cyanophenol, 2-chlorophenol, 3-chlorophenol,
4-chlorophenol, 2,4-dichlorophenol, 2,5-dichlorophenol, 2,6-dichlorophenol,
3,4-dichlorophenol, 3,5-dichlorophenol, 2,4,6-trichlorophenol,
2,4,5-trichlorophenol, pentachlorophenol, 2-fluorophenol, 3-fluorophenol,
4-fluorophenol, 2,4-difluorophenol, 2,5-difluorophenol, 2,6-difluorophenol,
3,4-difluorophenol, 3,5-difluorophenol, 2,4,6-trifluorophenol,
2,4,5-trifluorophenol, pentafluorophenol, 2-bromophenol, 3-bromophenol,
4-bromophenol, 2,4-dibromophenol, 2,5-dibromophenol, 2,6-dibromophenol,
3,4-dibromophenol, 3,5-dibromophenol, 2,4,6-tribromophenol,
2,4,5-tribromophenol, pentabromophenol, 2-hydroxybenzaldehyde,
3-hydroxybenzaldehyde, 4-hydroxybenzaldehyde, 2-hydroxyacetophenone,
3-hydroxyacetophenone, 4-hydroxyacetophenone, 2-hydroxybenzophenone,
3-hydroxybenzophenone, 4-hydroxybenzophenone, 2-trifluoromethylphenol,
3-trifluoromethylphenol, 4-trifluoromethylphenol, 2-trichloromethylphenol,
3-trichloromethylphenol, 4-trichloromethylphenol, 2-trifluoromethoxyphenol,
3-trifluoromethoxyphenol, 4-trifluoromethoxyphenol,
2-trichloromethoxyphenol, 3-trichloromethoxyphenol,
4-trichloromethoxyphenol, 2-hydroxyphenylmethylsulfone,
3-hydroxyphenylmethylsulfone,
4-hydroxyphenylmethylsulfone,
2-hydroxydiphenylsulfone, 4-hydroxydiphenylsulfone,
4-hydroxyphenylmethylsulfoxide,
4-hydroxydiphenylsulfoxide,
4-hydroxyphenylmethylsulfide, 4-hydroxydiphenylsulfide,
(B) $X_1$ is a substituent of group (b) in the formula (1):
2,2'-dihydroxydiphenylsulfone, 2,3'-dihydroxydiphenylsulfone,
2,4'-dihydroxydiphenylsulfone, 3,3'-dihydroxydiphenylsulfone,
3,4'-dihydroxydiphenylsulfone, 4,4'-dihydroxydiphenylsulfone,
4-methyl-4'-hydroxydiphenylsulfone, 4-methoxy-4'-hydroxydiphenylsulfone,
4-phenyl-4'-hydroxydiphenylsulfone, 4-nitro-4'-hydroxydiphenylsulfone,
4-cyano-4'-hydroxydiphenylsulfone, 4-chloro-4'-hydroxydiphenylsulfone,
4-bromo-4'-hydroxydiphenylsulfone, 4-acetyl-4'-hydroxydiphenylsulfone,
4-benzoyl-4'-hydroxydiphenylsulfone,
4-trifluoromethyl-4'-hydroxydiphenylsulfone,
4-trichloromethyl-4'-hydroxydiphenylsulfone,
4-trifluoromethoxy-4'-hydroxydiphenylsulfone,
4-trichloromethoxy-4'-hydroxydiphenylsulfone,
4-methylsulfonyl-4'-hydroxydiphenylsulfone,
4-phenylsulfonyl-4'-hydroxydiphenylsulfone,
2,2'-dihydroxydiphenylsulfoxide, 2,3'-dihydroxydiphenylsulfoxide,
2,4'-dihydroxydiphenylsulfoxide, 3,3'-dihydroxydiphenylsulfoxide,
3,4'-dihydroxydiphenylsulfoxide, 4,4'-dihydroxydiphenylsulfoxide,
4-methyl-4'-hydroxydiphenylsulfoxide,
4-methoxy-4'-hydroxydiphenylsulfoxide,
4-phenyl-4'-hydroxydiphenylsulfoxide, 4-nitro-4'-hydroxydiphenylsulfoxide,
4-cyano-4'-hydroxydiphenylsulfoxide, 4-chloro-4'-hydroxydiphenylsulfoxide,
4-bromo-4'-hydroxydiphenylsulfoxide, 4-acetyl-4'-hydroxydiphenylsulfoxide,
4-benzoyl-4'-hydroxydiphenylsulfoxide,
4-trifluoromethyl-4'-hydroxydiphenylsulfoxide,
4-trichloromethyl-4'-hydroxydiphenylsulfoxide,
4-trifluoromethoxy-4'-hydroxydiphenylsulfoxide,
4-trichloromethoxy-4'-hydroxydiphenylsulfoxide,
2,2'-dihydroxydiphenylsulfide, 2,3'-dihydroxydiphenylsulfide,
2,4'-dihydroxydiphenylsulfide, 3,3'-dihydroxydiphenylsulfide,
3,4'-dihydroxydiphenylsulfide, 4,4'-dihydroxydiphenylsulfide,
4-methyl-4'-hydroxydiphenylsulfide, 4-methoxy-4'-hydroxydiphenylsulfide,
4-phenyl-4'-hydroxydiphenylsulfide, 4-nitro-4'-hydroxydiphenylsulfide,
4-cyano-4'-hydroxydiphenylsulfide, 4-chloro-4'-hydroxydiphenylsulfide,
4-bromo-4'-hydroxydiphenylsulfide, 4-acetyl-4'-hydroxydiphenylsulfide,
4-benzoyl-4'-hydroxydiphenylsulfide,
4-trifluoromethyl-4'-hydroxydiphenylsulfide,
4-trichloromethyl-4'-hydroxydiphenylsulfide,
4-trifluoromethoxy-4'-hydroxydiphenylsulfide,
4-trichloromethoxy-4'-hydroxydiphenylsulfide,
2,2'-dihydroxydiphenylether, 2,3'-dihydroxydiphenylether,
2,4'-dihydroxydiphenylether, 3,3'-dihydroxydiphenylether,
3,4'-dihydroxydiphenylether, 4,4'-dihydroxydiphenylether,
4-methyl-4'-hydroxydiphenylether, 4-methoxy-4'-hydroxydiphenylether,
4-phenyl-4'-hydroxydiphenylether, 4-nitro-4'-hydroxydiphenylether,
4-cyano-4'-hydroxydiphenylether, 4-chloro-4'-hydroxydiphenylether,
4-bromo-4'-hydroxydiphenylether, 4-acetyl-4'-hydroxydiphenylether,
4-benzoyl-4'-hydroxydiphenylether,
4-trifluoromethyl-4'-hydroxydiphenylether,
4-trichloromethyl-4'-hydroxydiphenylether,
4-trifluoromethoxy-4'-hydroxydiphenylether,
4-trichloromethoxy-4'-hydroxydiphenylether,
4-methylsulfonyl-4'-hydroxydiphenylether,
4-phenylsulfonyl-4'-hydroxydiphenylether,
2,2'-dihydroxybenzophenone, 2,3'-dihydroxybenzophenone,
2,4'-dihydroxybenzophenone, 3,3'-dihydroxybenzophenone,
3,4'-dihydroxybenzophenone, 4,4'-dihydroxybenzophenone,
4-methyl-4'-hydroxybenzophenone, 4-methoxy-4'-hydroxybenzophenone,
4-phenyl-4'-hydroxybenzophenone, 4-nitro-4'-hydroxybenzophenone, 4-cyano-4'-hydroxybenzophenone, 4-chloro-4'-hydroxybenzophenone,
4-bromo-4'-hydroxybenzophenone, 4-acetyl-4'-hydroxybenzophenone,
4-benzoyl-4'-hydroxybenzophenone,
4-trifluoromethyl-4'-hydroxybenzophenone,
4-trichloromethyl-4'-hydroxybenzophenone,
4-trifluoromethoxy-4'-hydroxybenzophenone,
4-trichloromethoxy-4'-hydroxybenzophenone,
4-methylsulfonyl-4'-hydroxybenzophenone,
4-phenylsulfonyl-4'-hydroxybenzophenone,
2,2'-dihydroxydiphenylmethane, 2,3'-dihydroxydiphenylmethane,
2,4'-dihydroxydiphenylmethane, 3,3'-dihydroxydiphenylmethane,
3,4'-dihydroxydiphenylmethane, 4,4'-dihydroxydiphenylmethane,
4-methyl-4'-hydroxydiphenylmethane,
4-methoxy-4'-hydroxydiphenylmethane,
4-phenyl-4'-hydroxydiphenylmethane,
4-nitro-4'-hydroxydiphenylmethane, 4-cyano-4'-hydroxydiphenylmethane,
4-chloro-4'-hydroxydiphenylmethane, 4-bromo-4'-hydroxydiphenylmethane,
4-acetyl-4'-hydroxydiphenylmethane, 4-benzoyl-4'-hydroxydiphenylmethane,
4-trifluoromethyl-4'-hydroxydiphenylmethane,
4-trichloromethyl-4'-hydroxydiphenylmethane,
4-trifluoromethoxy-4'-hydroxydiphenylmethane,
4-trichloromethoxy-4'-hydroxydiphenylmethane,
4-methylsulfonyl-4'-hydroxydiphenylmethane,
4-phenylsulfonyl-4'-hydroxydiphenylmethane,
2,2-bis(2-hydroxyphenyl) propane,
2-(2-hydroxyphenyl)-2-(3-hydroxyphenyl) propane,
2-(2-hydroxyphenyl)-2-(4-hydroxyphenyl) propane,
2,2-bis(3-hydroxyphenyl) propane,
2-(3-hydroxyphenyl)-2-(4-hydroxyphenyl) propane,
2,2-bis(4-hydroxyphenyl) propane,
2-(4-methylphenyl)-2-(4-hydroxyphenyl) propane,
2-(4-methoxyphenyl)-2-(4-hydroxyphenyl) propane,
2-(4-phenylphenyl)-2-(4-hydroxyphenyl) propane,
2-(4-nitrophenyl) 2-(4-hydroxyphenyl) propane,
2-(4-cyanophenyl)-2-(4-hydroxyphenyl) propane,
2-(4-chlorophenyl)-2-(4-hydroxyphenyl) propane,
2-(4-acetylphenyl)-2-(4-hydroxyphenyl) propane,
2-(4-benzoylphenyl)-2-(4-hydroxyphenyl) propane,
2-(4-trifluoromethylphenyl)-2-(4-hydroxyphenyl) propane,
2-(4-trichloromethylphenyl)-2-(4-hydroxyphenyl) propane,
2-(4-trifluoromethoxyphenyl)-2-(4-hydroxyphenyl) propane,
2-(4-trichloromethoxyphenyl)-2-(4-hydroxyphenyl) propane,
2-(4-trimethylsulfonylphenyl)-2-(4-hydroxyphenyl) propane,
2-(4-phenylsulfonylphenyl)-2-(4-hydroxyphenyl) propane,
2-(4-trifluoromethylphenyl)-2-(4-hydroxyphenyl) propane,
2,2-bis(2-hydroxyphenyl)-1,1,1,3,3,3-hexafluoropropane,
2-(2-hydroxyphenyl)-2-(3-hydroxyphenyl)-1,1,1,3,3,3-hexafluoropropane,
2-(2-hydroxyphenyl)-2-(4-hydroxyphenyl)-1,1,1,3,3,3-hexafluoropropane,
2,2-bis(3-hydroxyphenyl)-1,1,1,3,3,3-hexafluoropropane,
2-(3-hydroxyphenyl)-2-(4-hydroxyphenyl)-1,1,1,3,3,3-hexafluoropropane,
2,2-bis(4-hydroxyphenyl)-1,1,1,3,3,3-hexafluoropropane,
2-(4-methylphenyl)-2-(4-hydroxyphenyl)-1,1,1,3,3,3hexafluoropropane,
2-(4-methoxyphenyl)-2-(4-hydroxyphenyl)-1,1,1,3,3,3-hexafluoropropane,
2-(4-phenylphenyl)-2-(4-hydroxyphenyl)-1,1,3,3,3-hexafluoropropane,
2-(4-nitrophenyl)-2-(4-hydroxyphenyl)-1,1,1,3,3,3-hexafluoropropane,
2-(4-cyanophenyl)-2-(4-hydroxyphenyl)-1,1,1,3,3,3-hexafluoropropane,
2-(4-chlorophenyl)-2-(4-hydroxyphenyl)-1,1,1,3,3,3-hexafluoropropane,
2-(4-acetylphenyl)-2-(4-hydroxyphenyl)-1,1,1,3,3,3-hexafluoropropane,
2-(4-benzoylphenyl)-2-(4-hydroxyphenyl)-1,1,3,3,3-hexafluoropropane,
2-(4-trifluoromethylphenyl)-2-(4-hydroxyphenyl)-1 1,1,3,3,3-hexafluoropropane,
2-(4-trichloromethylphenyl)-2-(4-hydroxyphenyl)-1,1,3,3,3-hexafluoropropane,
2-(4-trifluoromethoxyphenyl)-2-(4-hydroxyphenyl)-1,1,1,3,3,3-hexafluoropropane,
2-(4-trichloromethoxyphenyl)-2-(4-hydroxyphenyl)-1,1,1,3,3,3-hexafluoropropane,
2-(4-methylsulfonylphenyl)-2-(4-hydroxyphenyl)-1,1,1,3,3,3-hexafluoropropane,
2-(4-phenylsulfonylphenyl)-2-(4-hydroxyphenyl)-1,1,1,3,3,3-hexafluoropropane,
2,2'-dihydroxybiphenyl, 2,3'-dihydroxybiphenyl, 2,4'-dihydroxybiphenyl,
3,3'-dihydroxybiphenyl, 3,4'-dihydroxybiphenyl, 4,4'-dihydroxybiphenyl,
4-methyl-4'-hydroxybiphenyl, 4-methoxy-4'-hydroxybiphenyl,
4-phenyl-4'-hydroxybiphenyl, 4-nitro-4'-hydroxybiphenyl,
4-cyano-4'-hydroxybiphenyl, 4-chloro-4'-hydroxybiphenyl,
4-bromo-4'-hydroxybiphenyl, 4-acetyl-4'-hydroxybiphenyl,
4-benzoyl-4'-hydroxybiphenyl, 4-trifluoromethyl-4'-hydroxybiphenyl,
4-trichloromethyl-4'-hydroxybiphenyl,
4-trifluoromethoxy-4'-hydroxybiphenyl,
4-trichloromethoxy-4'-hydroxybiphenyl,
4-methylsulfonyl-4'-hydroxybiphenyl,
4-phenylsulfonyl-4'-hydroxybiphenyl,
(C) $X_1$ is a substituent of group (c) in the formula (1):
2-hydroxyphenyltrifluoromethylsulfone,
3-hydroxyphenyltrifluoromethylsulfone,
4-hydroxyphenyltrifluoromethylsulfone,
2-hydroxyphenyltrichloromethylsulfone,
3-hydroxyphenyltrichloromethylsulfone,
4-hydroxyphenyltrichloromethylsulfone,
4-hydroxyphenyltrifluoromethylsulfoxide,
4-hydroxyphenyltrichloromethylsulfoxide,
4-hydroxyphenyltrifluoromethylsulfide,
4-hydroxyphenyltrichloromethylsulfide,
2-hydroxyphenyltrifluoromethylketone,
3-hydroxyphenyltrifluoromethylketone,
4-hydroxyphenyltrifluoromethylketone,
2-hydroxyphenyltrichloromethylketone,
3-hydroxyphenyltrichloromethylketone,
4-hydroxyphenyltrichloromethylketone.

Alkali metal or alkali earth metal salt of various hydroxy compounds is included. However, the invention is not limited by these exemplified compounds.

Preferred compounds are an alkali metal or alkali earth metal salt of substituted hydroxybenzene represented by the formula (1-1):

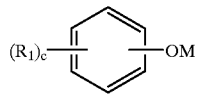
(1-1)

wherein M, $R_1$ and c are the same as above, an alkali metal or alkali earth metal salt of hydroxy benzophenone represented by the formula (1-2):

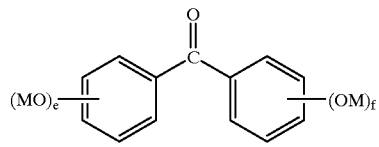
(1-2)

wherein e and f are an integer of 0 to 5, and can be the same or different, however, f is 1 or more when e is 0, and e is 1 or more when f is 0, and M is an alkali metal or alkali earth metal atom, and an alkali metal or alkali earth metal salt of hydroxy diaryl sulfone represented by the formula (1-3):

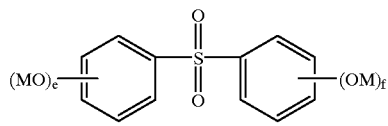
(1-3)

wherein e, f and M are the same as the formula (1-2).

The alkali metal or alkali earth metal salt of hydroxy compound which can be used in the invention and represented by the formula (1) can be prepared by reacting the corresponding hydroxy compound with an alkali metal or alkali earth metal base (hereinafter referred to simply as base).

The reaction is carried out in an aqueous solution, successively benzene, toluene, xylene or other inert solvent is added and water is azeotropically distilled off to isolate the resulting salt.

Representative organic fluorinating agents which can be used in the invention include, for example, N,N-diethyl(1,1,2-trifluoro-2-chloroethyl)amine, N,N-diethyl(1,1,2,3,3,3-hexafluoroethyl)amine and other fluoroalkylamine reagents; 1-dimethylamino-1-fluoro-2-methylpropane, 1-diethylamino-1-fluoro-2-methylpropane and other fluoroenamine type fluorinating agent;triphenylphosphine difluoride, phenylphosphine tetrafluoride and other fluorophenylphosphorenes; and diethylaminosulfur trifluoride, a compound represented by the formula (5);

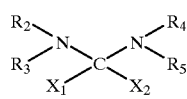
(5)

wherein $R_2$, $R_3$, $R_4$ and $R_5$ are an alkyl or aryl group having 1 to 6 carbon atoms and can be the same or different, $R_2$ and $R_3$ or $R_4$ and $R_5$ can bond to form a ring having one or more nitrogen atoms or having one or more nitrogen atoms and other hetero atoms, $R_2$ and $R_4$ can bond to form a ring having one or more nitrogen atoms or having one or more nitrogen atoms and other hetero atoms, and $X_1$ is a fluorine atom, $X_2$ is a fluorine or chlorine atom, and $X_1$ and $X_2$ can form a covalent bond respectively with a carbon atom or $X_1$ alone can form a covalent bond and $X_2$ can exist in the form of an ion pair;

preferably a compound, bis-dialkylamino difluoromethane, represented by the formula (5-1);

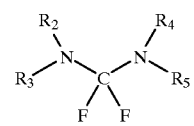
(5-1)

wherein $R_2$, $R_3$, $R_4$ and $R_5$ are the same as the formula (5); and more preferably 2,2-difluoro-1,3-dimethylimidazolidine having the formula (5-2);

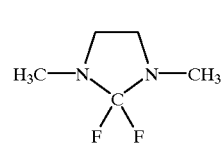
(5-2)

In the formula (5), the substituent represented by $R_2$, $R_3$, $R_4$ and $R_5$ are alkyl or aryl groups having 1 to 6 carbon atoms and include, for example, a, methyl, ethyl, n-propyl, isopropyl, n-butyl, n-pentyl, n-hexyl and phenyl group.

$R_2$ and $R_4$ in the formula can bond together to form a five or six membered ring. Alternatively, $R_2$ and $R_3$ or $R_4$ and $R_5$ can respectively bond each other to form a heterocyclic ring having a nitrogen atom and 3 to 5 carbon atoms.

Representative compounds represented by the formula (5) include, for example,
bis-dimethylamino-difluoromethane, bis-diethylamino-difluoromethane,
bis-dipropylamino-difluoromethane, bis-di-isopropylamino-difluoromethane,
bis-di-n-butylamino-difluoromethane, bis-di-isobutylamino-difluoromethane,
bis-di-tert-butylamino-difluoromethane,
bis-di-n-pentylamino-difluoromethane, bis-di-n-hexylamino-difluoromethane,
2,2-difluoro-1,3-dimethyl-imidazolidine,
2,2-difluoro-1-ethyl-3-methyl-imidazolidine,
2,2-difluoro-1,3-diethyl-imidazolidine,
2,2-difluoro-1,3-di-n-propyl-imidazolidine
2,2-difluoro-1,3-diisopropyl-imidazolidine,
2,2-difluoro-1,3-di-n-butyl-imidazolidine,
N,N-dimethyl-N'-methyl-N'-phenyl-difluoromethane, and bis-piperidyl-difluoromethane. However, the invention is not limited by these examples.

Exemplary hetero rings resulting from bonding $R_2$ and $R_3$ or $R_4$ and $R_5$ respectively and having nitrogen atoms, preferably having 3 to 5 carbon atom include a pyrrolidine ring and piperidine ring.

Exemplary five membered or six membered hetero rings resulting from bonding of $R_2$ and $R_4$ and having two nitrogen atoms include an imidazolidine ring, pyrimidine ring and pyrimidinone ring.

These compounds can be prepared by reaction of an alkali metal salt of fluorine and tetraalkyl-chloroformamidinium=chloride represented by the formula (6);

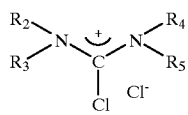

(6)

wherein $R_2$, $R_3$, $R_4$ and $R_5$ are an alkyl or aryl group having 1 to 6 carbon atoms and can be the same or different, $R_2$ and $R_3$ or $R_4$ and $R_5$ can bond to form a ring having one or more nitrogen atoms or having one or more nitrogen atoms and other hetero atoms, $R_2$ and $R_3$ can bond to form a ring having one or more nitrogen atoms or having one or more nitrogen atoms and other hetero atoms.

Exemplary alkali metal salts of fluorine which can be used include, for example, cesium fluoride, rubidium fluoride, potassium fluoride and sodium fluoride. Spray dried potassium fluoride for fluorination reaction can be preferably used in view of economy and reaction efficiency. The compound of the formula (6) can be obtained in safety and with ease by carrying out the halogen exchange reaction in a solvent.

On preparation of a compound having a chlorine ion pair in the formula(5), the amount of alkali metal salt of fluorine used in the halogen exchange reaction is usually one mole or more, preferably 1 to 1.5 mole for one mole of the compound represented by the formula (6). When the amount is less than one mole, unreacted chloride remains after the reaction. The amount exceeding 1.5 mol tends to increase formation of difluoro compound.

However, contamination of difluoro compound causes no problem at all on the preparation of substituted fluorobenzene.

No particular restriction is imposed upon the reaction solvent as long as the solvent does not react with the compounds represented by the formulas (5) and (6).

Preferred solvents are acetonitrile, dimethylformamide, 1,3-dimethyl-2-imidazolidinone, dichloromethane and ethylene dichloride. No particular limitation is put upon the amount of solvent. Preferred amount is usually 1 to 10 times by weight for the reaction material in view of reaction efficiency and operation ability.

No particular limitation is imposed upon the reaction temperature. The reaction temperature is usually in the range of −20 to 150° C., preferably 0 to 100° C. in view of reaction velocity and stability of product.

The halogen exchange reaction for preparing the compound represented by the formula (5) can also be carried out in the presence of a phase transfer catalyst such as quaternary alkyl ammonium salt and quaternary alkyl phosphonium salt.

The resulting compound represented by the formula (5) can be used in the halogen exchange reaction mixture as intact for the next synthesis reaction of the fluorine substituted aromatic compound. The compound of the formula (5) can also be used after filtering off the inorganic salt from the reaction mixture, or can also be used after filtering off the inorganic salt and isolating by distillation or crystallization.

The compound represented by the formula (6) which can be used for preparing the compound represented by the formula (5) can be prepared by chlorinating tetraalkylurea, tetraalkylthiourea, 1,3-dialkylimidazolidinone, and 1,3-dialkylimidazolidine-2-thion with phosgene, thionyl chloride and other chlorinating agent.

For example, 2-chloro-1,3-dimethylimidazolidinium=chloride can be prepared with ease by the process described in Japanese Patent SHO 59-25375.

The amount of alkali metal salt of fluorine which is used for the halogen exchange reaction in the invention is two equivalents or more, preferably 2 to 5 equivalents for tetraalkyl chloroformamidinium=chloride. When the amount is less than 2 equivalents, unreacted chloride remains after the reaction. Use of more than 5 equivalents leads to no remarkable improvement on the reaction.

The fluorinating reaction of an alkali metal or alkali earth metal salt of the hydroxy compound represented by the formula (1) by using the above fluorinating agent will be described in detailed hereinafter.

The fluorinating agents which can be used are the above fluorinating agent, preferably bis-dialkylamino-difluoromethane represented by the formula (5), more preferably bis-dialkylaminodifluoromethane represented by the formula (5-1), most preferably 2,2-difluoro-1,3-dimethyl-imidazolidine represented by the formula (5-1).

The amount of the fluorinating agent is preferably 1 equivalent or more preferably 1 to 10 equivalents for the functional group (—OM in formula(1)) of the hydroxy compound represented by the formula(1) Unreacted hydroxyl group remains when the amount is less than 1 equivalent. Thus, when a compound having both hydroxyl and fluoro groups is desired, the amount is suitably adjusted in the range less than 1 equivalent.

No particular restriction is imposed upon the reaction solvent as long as the solvent is inert to the fluorinating agent, the alkali metal or alkali earth metal salt of hydroxy compound and fluorine substituted aromatic compound formed in the reaction.

Preferred solvents are acetonitrile, dichloromethane, chloroform, ethylene dichloride, N-methylpyrrolidinone, dimethylformamide and 1,3-dimethyl-2-imidazolidinone.

The reaction temperature is in the range of preferably 0 to 200° C., more preferably 40 to 150° C. When the temperature is less than 0° C., reaction velocity becomes slow and operation becomes complex. The temperature exceeding 200° C. lowers stability of the fluorinating agent.

The fluorine substituted aromatic compound formed by the reaction can be separated with ease from the reaction mixture by concentration or extraction. When bis-dialkylamino difluoromethane is used for fluorinating agent, the agent can be recovered after finishing the reaction in the form of tetraalkyl urea or 1,3-dialkylimidazolidinone.

The recovered compound can be converted to chloroformamidium=chloride represented by the formula (6) through chlorination by the above procedure. Successively, the resulting compound represented by the formula (6) can be subjected to a halogen exchange reaction with an alkali metal salt of fluorine. Thus, the compound represented by the formula(5) can be obtained again.

In the process of the invention, when the hydroxy aromatic compound is di-sodium salt or di-potassium salt of 4,4'-dihydroxybenzophenone or 4,4'-dihydroxydiphenyl sulfone, corresponding 4,4'-difluorobenzophenone or 4,4'-difluorodiphenyl sulfone can obtained as a product. In order to enhance selectivity, the fluorinating agent is preferably used in excess, that is, 2 to 10 equivalents. Further when bis-dialkylamino-difluoromethane is used as a fluorinating agent, di-sodium salt or di-potassium salt of 4,4'-dihydroxybenzophenone or 4,4'-dihydroxydiphenyl sulfone is preferably added dropwise into bis-di-alkylamino-difluoromethane.

By the process of the invention, the fluorine substituted aromatic compound represented by the following formula (4) which can respectively correspond to the formula (1) can be obtained.

(D) Fluorine substituted aromatic compound represented by the formula (4) corresponding to the hydroxy compound wherein $X_1$ is a substituent of the group (a) in the formula (1):

2-methylfluorobenzene, 3-methylfluorobenzene, 4-methylfluorobenzene,
2-ethylfluorobenzene, 3-ethylfluorobenzene, 4-ethylfluorobenzene,
2,3-dimethylfluorobenzene, 2,4-dimethylfluorobenzene, 2,5-dimethylfluorobenzene, 2,6-dimethylfluorobenzene, 3,4-dimethylfluorobenzene, 3,5-dimethylfluorobenzene,
2-methoxyfluorobenzene, 3-methoxyfluorobenzene, 4-methoxyfluorobenzene, 2-ethoxyfluorobenzene, 3-ethoxyfluorobenzene, 4-ethoxyfluorobenzene,
2,3-dimethoxyfluorobenzene, 2,6-dimethoxyfluorobenzene, 3,4-dimethoxyfluorobenzene, 3,5-dimethoxyfluorobenzene,
2-fluorobiphenyl, 3-fluorobiphenyl, 4-fluorobiphenyl,
2,6-diphenylfluorobenzene, 4-phenoxyfluorobenzene,
2-nitrofluorobenzene, 3-nitrofluorobenzene, 4-nitrofluorobenzene,
2,4-dinitrofluorobenzene, 2,5-dinitrofluorobenzene, 2,4,6-trinitrofluorobenzene,
2-cyanofluorobenzene, 3-cyanofluorobenzene, 4-cyanofluorobenzene,
2-chlorofluorobenzene, 3-chlorofluorobenzene, 4-chlorofluorobenzene,
2,4-dichlorofluorobenzene, 2,5-dichlorofluorobenzene, 2,6-dichlorofluorobenzene, 3,4-dichlorofluorobenzene, 3,5-dichlorofluorobenzene, 2,4,6-trichlorofluorobenzene, 2,4,5-trichlorofluorobenzene, pentachlorofluorobenzene,
1,2-difluorobenzene, 1,3-difluorobenzene, 1,4-difluorobenzene, 1,2,4-trifluorobenzene, 1,2,5-trifluorobenzene, 1,2,6-trifluorobenzene, 1,3,4-trifluorobenzene, 1,3,5-trifluorobenzene, 1,2,4,6-tetrafluorobenzene, 1,2,4,5-tetrafluorobenzene, hexafluorobenzene, 2-bromofluorobenzene, 3-bromofluorobenzene, 4-bromofluorobenzene, 2,4-dibromofluorobenzene, 2,5-dibromofluorobenzene, 2,6-dibromofluorobenzene, 3,4-dibromofluorobenzene, 3,5-dibromofluorobenzene, 2,4,6-tribromofluorobenzene, 2,4,5-trifluorobromofluorobenzene, pentabromofluorobenzene,
2-fluorobenzaldehyde, 3-fluorobenzaldehyde, 4-fluorobenzaldehyde,
2-fluoroacetophenone, 3-fluoroacetophenone, 4-fluoroacetophenone,
2-fluorobenzophenone, 3-fluorobenzophenone, 4-fluorobenzophenone,
2-trifluoromethylfluorobenzene, 3-trifluoromethylfluorobenzene, 4-trifluoromethylfluorobenzene, 2-trichloromethylfluorobenzene, 3-trichloromethylfluorobenzene, 4-trichloromethylfluorobenzene,
2-trifluoromethoxyfluorobenzene, 3-trifluoromethoxyfluorobenzene, 4-trifluoromethoxyfluorobenzene, 2-trichloromethoxyfluorobenzene, 3-trichloromethoxyfluorobenzene, 4-trichloromethoxyfluorobenzene,
2-fluorophenylmethylsulfone, 3-fluorophenylmethylsulfone, 4-fluorophenylmethylsulfone, 2-hydroxydiphenylsulfone, 4-hydroxydiphenylsulfone, 4-fluorophenylmethylsulfoxide, 4-fluorodiphenylsulfoxide, 4-fluorophenylmethylsulfide, 4-fluorodiphenylsulfide, (E) Fluorine substituted aromatic compound represented by the formula (4) corresponding to the hydroxy compound wherein $X_1$ is a substituent of the group (b) in the formula (1):

2,2'-difluorodiphenylsulfone, 2,3'-difluorodiphenylsulfone, 2,4'-difluorodiphenylsulfone, 3,3'-difluorodiphenylsulfone, 3,4'-difluorodiphenylsulfone, 4,4'-difluorodiphenylsulfone, 4-methyl-4'-fluorodiphenylsulfone, 4-methoxy-4'-fluorodiphenylsulfone,
4-phenyl-4'-fluorodiphenylsulfone, 4-nitro-4'-fluorodiphenylsulfone,
4-cyano-4'-fluorodiphenylsulfone, 4-chloro-4'-fluorodiphenylsulfone,
4-bromo-4'-fluorodiphenylsulfone, 4-acetyl-4'-fluorodiphenylsulfone,
4-benzoyl-4'-fluorodiphenylsulfone,
4-trifluoromethyl-4'-fluorodiphenylsulfone,
4-trichloromethyl-4'-fluorodiphenylsulfone,
4-trifluoromethoxy-4'-fluorodiphenylsulfone,
4-trichloromethoxy-4'-fluorodiphenylsulfone,
4-methylsulfonyl-4'-fluorodiphenylsulfone,
4-phenylsulfonyl-4'-fluorodiphenylsulfone,
2,2'-difluorodiphenylsulfoxide, 2,3'-difluorodiphenylsulfoxide,
2,4'-difluorodiphenylsulfoxide, 3,3'-difluorodiphenylsulfoxide,
3,4'-difluorodiphenylsulfoxide, 4,4'-difluorodiphenylsulfoxide,
4-methyl-4'-fluorodiphenylsulfoxide, 4-methoxy-4'-fluorodiphenylsulfoxide,
4-phenyl-4'-fluorodiphenylsulfoxide, 4-nitro-4'-fluorodiphenylsulfoxide,
4-cyano-4'-fluorodiphenylsulfoxide, 4-chloro-4'-fluorodiphenylsulfoxide,
4-bromo-4'-hydroxydiphenylsulfoxide, 4-acetyl-4'-fluorodiphenylsulfoxide,
4-benzoyl-4'-fluorodiphenylsulfoxide,
4-trifluoromethyl-4'-fluorodiphenylsulfoxide,
4-trichloromethyl-4'-fluorodiphenylsulfoxide,
4-trifluoromethoxy-4'-fluorodiphenylsuloxide,
4-trichloromethoxy-4'-fluorodiphenylsulfoxide,
2,2'-difluorodiphenylsulfide, 2,3'-difluorodiphenylsulfide,
2,4'-difluorodiphenylsulfide, 3,3'-difluorodiphenylsulfide,
3,4'-difluorodiphenylsulfide, 4,4'-difluorodiphenylsulfide,
4-methyl-4'-fluorodiphenylsulfide, 4-methoxy-4'-fluorodiphenylsulfide,
4-phenyl-4'-fluorodiphenylsulfide, 4-nitro-4'-fluorodiphenylsulfide,
4-cyano-4'-fluorodiphenylsulfide, 4-chloro-4'-fluorodiphenylsulfide,
4-bromo-4'-fluorodiphenylsulfide, 4-acetyl-4'-fluorodiphenylsulfide,
4-benzoyl-4'-fluorodiphenylsulfide, 4-trifluoromethyl-4'-fluorodiphenylsulfide,
4-trichloromethyl-4'-fluorodiphenylsulfide,
4-trifluoromethoxy-4'-fluorodiphenylsulfide,
4-trichloromethoxy-4'-fluorodiphenylsulfide,
2,2'-difluorodiphenylether, 2,3'-difluorodiphenylether,
2,4'-difluorodiphenylether, 3,3'-difluorodiphenylether,
3,4'-difluorodiphenylether, 4,4'-difluorodiphenylether,
4-methyl-4'-fluorodiphenylether, 4-methoxy-4'-fluorodiphenylether,
4-phenyl-4'-fluorodiphenylether, 4-nitro-4'-fluorodiphenylether,
4-cyano-4'-fluorodiphenylether, 4-chloro-4'-fluorodiphenylether,
4-bromo-4'-fluorodiphenylether, 4-acetyl-4'-fluorodiphenylether, 4-benzoyl-4'-fluorodiphenylether, 4-trifluoromethyl-4'-fluorodiphenylether,
4-trichloromethyl-4'-fluorodiphenylether,
4-trifluoromethoxy-4'-fluorodiphenylether,
4-trichloromethoxy-4'-fluorodiphenylether,
4-methylsulfonyl-4'-fluorodiphenylether,
4-phenylsulfonyl-4'-fluorodiphenylether,
2,2'-difluorobenzophenone, 2,3'-difluorobenzophenone,
2,4'-difluorobenzophenone, 3,3'-difluorobenzophenone,
3,4'-difluorobenzophenone, 4,4'-difluorobenzophenone,
4-methyl-4'-fluorobenzophenone, 4-methoxy-4'-fluorobenzophenone,
4-phenyl-4'-fluorobenzophenone, 4-nitro-4'-fluorobenzophenone,
4-cyano-4'-fluorobenzophenone, 4-chloro-4'-fluorobenzophenone,
4-bromo-4'-fluorobenzophenone, 4-acetyl-4'-fluorobenzophenone,
4-benzoyl-4'-fluorobenzophenone, 4-trifluoromethyl-4'-fluorobenzophenone,
4-trichloromethyl-4'-fluorobenzophenone,
4-trifluoromethoxy-4'-fluorobenzophenone,
4-trichloromethoxy-4'-fluorobenzophenone,
4-methylsulfonyl-4'-fluorobenzophenone,
4-phenylsulfonyl-4'-fluorobenzophenone,
2,2'-difluorodiphenylmethane, 2,3'-difluorodiphenylmethane,
2,4'-difluorodiphenylmethane, 3,3'-difluorodiphenylmethane,
3,4'-difluorodiphenylmethane, 4,4'-difluorodiphenylmethane,
4-methyl-4'-fluorodiphenylmethane, 4-methoxy-4'-fluorodiphenylmethane,
4-phenyl-4'-fluorodiphenylmethane, 4-nitro-4'-fluorodiphenylmethane,
4-cyano-4'-fluorodiphenylmethane, 4-chloro-4'-fluorodiphenylmethane,
4-bromo-4'-fluorodiphenylmethane, 4-acetyl-4'-fluorodiphenylmethane,
4-benzoyl-4'-fluorodiphenylmethane,
4-trifluoromethyl-4'-fluorodiphenylmethane,
4-triehloromethyl-4'-fluorodiphenylmethane,
4-trifluoromethoxy-4'-fluorodiphenylmethane,
4-trichloromethoxy-4'-fluorodiphenylmethane,
4-methylsulfonyl-4'-fluorodiphenylmethane,
4-phenylsulfonyl-4'-fluorodiphenylmethane,
2,2-bis(2-fluorophenyl) propane,
2-(2-fluorophenyl)-2-(3-fluorophenyl) propane,
2-(2-fluorophenyl)-2-(4-fluorophenyl) propane,
2,2-bis(3-fluorophenyl) propane,
2-(3-fluorophenyl)-2-(4-fluorophenyl) propane,
2,2-bis(4-fluorophenyl) propane,
2-(4-methylphenyl)-2-(4-fluorophenyl) propane,
2-(4-methoxyphenyl)-2-(4-fluorophenyl) propane,
2-(4-phenylphenyl)-2-(4-fluorophenyl) propane,
2-(4-nitrophenyl)-2-(4-fluorophenyl) propane,
2-(4-cyanophenyl)-2-(4-fluorophenyl) propane,
2-(4-chlorophenyl)-2-(4-fluorophenyl) propane,
2-(4-acetylphenyl)-2-(4-fluorophenyl) propane,
2-(4-benzoylphenyl)-2-(4-fluorophenyl) propane,
2-(4-trifluoromethylphenyl)-2-(4-fluorophenyl) propane,
2-(4-trichloromethylphenyl)-2-(4-fluorophenyl) propane,
2-(4-trifluoromethoxyphenyl)-2-(4-fluorophenyl) propane,
2-(4-trichloromethoxyphenyl)-2-(4-fluorophenyl) propane,
2-(4-methylsulfonylphenyl)-2-(4-fluorophenyl) propane,
2-(4-phenylsulfonylphenyl)-2-(4-fluorophenyl) propane,
2,2-bis(2-fluorophenyl)-1,1,1,3,3,3-hexafluoropropane,
2-(2-fluorophenyl)-2-(3-fluorophenyl)-1,1,1,3,3,3-hexafluoropropane,
2-(2-fluorophenyl)-2-(4-fluorophenyl)-1,1,1,3,3,3-hexafluoropropane,
2,2-bis(3-fluorophenyl)-1,1,1,3,3,3-hexafluoropropane,
2-(3-fluorophenyl)-2-(4-fluorophenyl)-1,1,1,3,3,3-hexafluoropropane,
2,2-bis(4-fluorophenyl)-1,1,1,3,3,3-hexafluoropropane,
2-(4-methylphenyl)-2-(4-fluorophenyl)-1,1,1,3,3,3-hexafluoropropane,
2-(4-methoxyphenyl)-2-(4-fluorophenyl)-1,1,1,3,3,3-hexafluoropropane,
2-(4-phenylphenyl)-2-(4-fluorophenyl)-1,1,1,3,3,3-hexafluoropropane,
2-(4-nitrophenyl)-2-(4-fluorophenyl)-1,1,1,3,3,3-hexafluoropropane,
2-(4-cyanophenyl)-2-(4-fluorophenyl)-1,1,1,3,3,3-hexafluoropropane,
2-(4-chlorophenyl)-2-(4-fluorophenyl)-1,1,1,3,3,3-hexafluoropropane,
2-(4-acetylphenyl)-2-(4-fluorophenyl)-1,1,1,3,3,3-hexafluoropropane,
2-(4-benzoylphenyl)-2-(4-fluorophenyl)-1,1,1,3,3,3-hexafluoropropane,
2-(4-trifluoromethylp henyl)-2-(4-fluorophenyl)-1,1,1,3,3,3-hexafluoropropane,
2-(4-trichloromethylphenyl)-2-(4-fluorophenyl)-1,1,1,3,3,3-hexafluoropropane,
2-(4-trifluoromethoxyphenyl)-2-(4-fluorophenyl)-1,1,1,3,3,3-hexafluoropropane,
2-(4-trichloromethoxyphenyl)-2-(4-fluorophenyl)-1,1,1,3,3,3-hexafluoropropane,
2-(4-methylsulfonylphenyl)-2-(4-fluorophenyl)-1,1,1,3,3,3-hexafluoropropane,
2-(4-sulfonylsulfonylphenyl)-2-(4-fluorophenyl)-1,1,1,3,3,3-hexafluoropropane,
(F) Fluorine substituted aromatic compound represented by the formula (4) corresponding to the hydroxy compound wherein $X_1$ is a substituent of the group (c) in the formula (1):
2,2'-difluorobiphenyl, 2,3'-difluorobiphenyl, 2,4'-difluorobiphenyl,
3,3'-difluorobiphenyl, 3,4'-difluorobiphenyl, 4,4'-difluorobiphenyl,
4-methyl-4'-fluorobiphenyl, 4-methoxy-4'-fluorobiphenyl,
4-phenyl-4'-fluorobiphenyl, 4-nitro-4'-fluorobiphenyl,
4-cyano-4'-fluorobiphenyl, 4-chloro-4'-fluorobiphenyl,
4-bromo-4'-fluorobiphenyl, 4-acetyl-4'-fluorobiphenyl,
4-benzoyl-4'-fluorobiphenyl, 4-trifluoromethyl-4'-fluorobiphenyl,
4-trichloromethyl-4'-fluorobiphenyl, 4-trifluoromethoxy-4'-fluorobiphenyl,
4-trichloromethoxy-4'-fluorobiphenyl, 4-methylsulfonyl-4'-fluorobiphenyl,
4-phenylsulfonyl-4'-fluorobiphenyl,
2-fluorophenyltrifluoromethylsulfone,
3-fluorophenyltrifluoromethylsulfone,
4-fluorophenyltrifluoromethylsulfone,
2-fluorophenyltrichloromethylsulfone,
3-fluorophenyltrichloromethylsulfone,
4-fluorophenyltrichloromethylsulfone,
4-fluorophenyltrifluoromethylsulfoxide,
4-fluorophenyltrichloromethylsulfoxide,
4-fluorophenyltrifluoromethylsulfide,
4-fluorophenyltrichloromethylsulfide,
2-fluorophenyltrifluoromethylketone,
3-fluorophenyltrifluoromethylketone, 4-fluorophenyltrifluoromethylketone,
2-fluorophenyltrichloromethylketone,
3-fluorophenyltrichloromethylketone,
4-fluorophenyltrichloromethylketone,

EXAMPLE

The invention will hereinafter be illustrated further in detailed by way of examples.

However, these examples are not to be construed to limit the scope of the invention. The concentration of 2,2-difluoro-1,3-dimethyimidazolidine (hereinafter referred to simply as DFI) in the acetonitrile solution of Synthesis Example 1 was measured by high performance chromatography (hereinafter referred to simply as HPLC) after converted to a derivative by reaction of DFI with aniline.

The concentration of fluorine ion (hereinafter referred to simply as F-) was measured by absorptiometry using a lanthanum alizarin complexon reagent.

Synthesis Example 1

Synthesis of 2,2-difluoro-1,3-dimethylimidazolidine (DFI)

To a 500 ml four-necked reaction flask, 80.0 g (0.452 mol) of 2-chloro-1,3-dimethylimidiazolidinium=chloride, 105.1 g (1.810 mol) of spray-dried potassium fluoride, and 320 ml acetonitrile were charged and reacted at 80° C. for 17 hours in a nitrogen atmosphere. The reaction mass was cooled to 25° C. and the inorganic salt was separated from the reaction mass. The acetonitrile solution of DFI (molecular weight: 136.14) thus obtained was 414.2 g. The concentration of DFI in the acetonitrile was 11.4 wt %. The solution was distilled under reduced pressure to obtain 32 g of DFI having purity of 97.8%. The yield w as 77%. DFI obtained had following properties.

Boiling point: 47.0° C./37 mmHg, FIMS: 136($M^+$), 117 ($M^+$-F), IR(neat) $cm^{-1}$: 1486, 1385, 1295, 1242, 1085, 966, F-analysis : calculated 27.9%, found 27.7%, $^1$H-NMR($\delta$, ppm, $CDCl_3$, TMS reference): 2.52 (s, 6H, —$CH_3$×2), 3.05 (s, 4H, —$CH_2$—$CH_2$—), 128.5(t, J=230 Hr), =$CF_2$), $^{13}$C-NMR($\delta$, ppm, $CDCl_3$, -45° C., $CDCl_3$ reference): 31.4 (s,—$CH_3$×2), 47.6(s, —$CH_2$—$CH_2$—), 128.5 (t, J=230 Hz,= $CF_2$), $^{19}$F-NMR($\delta$, ppm, $CDCl_3$, -45° C., $CDCl_3$ reference): −70.9(s, =$CF_2$).

Synthesis Example 2

Synthesis of potassium salt of p-nitrophenol

To a 500 ml four necked flask equipped with a Dean Stark trap, 27.8 g (0.2 mol) of p-nitrophenol and 82.5 g (0.2 mol) of a 13.6 wt % aqueous potassium hydroxide solution were charged and reacted at 30° C. for 30 minutes in a nitrogen atmosphere. Successively, 300 g of toluene was added and heated in a nitrogen atmosphere while separating the distilled water-toluene mixture in the Dean Stark trap and returning toluene alone to the reaction flask. After reaching the internal temperature to 110° C., the reaction was continued for 2 hours at the same temperature. The resulting toluene slurry of p-nitrophenol potassium salt was filtered and dried at 160° C. under 5.33 kPa(40 mmHg) for 4 hours to obtained 34.4 g of p-nitrophenol potassium salt. The yield was 97%.

Synthesis Example 3

Synthesis of di-potassium salt of 4,4'-dihydroxybenzophenone.

To a 1000 ml four-necked flask equipped with a Dean Stark trap, 42.8 g (0.2 mol) of dihydroxybenzophenone and 165 g (0.4 mol) of a 13.6 wt % aqueous potassium hydroxide solution were charged and reacted at 30° C. for 30 minutes.

Successively, 500 g of toluene was added and heated in a nitrogen atmosphere while separating the distilled water-toluene mixture in the Dean Stark trap and returning toluene alone to the reaction flask. After reaching the internal temperature to 110° C., the reaction was continued for 2 hours at the same temperature. The resulting toluene slurry of 4,4'-dihydroxybenzophenone di-potassium salt was filtered and dried at 160° C. under 5.33 kPa (40 mmHg) for 4 hours to obtain 56.9 g of 4,4'-dihydroxybenzophenone di-potassium salt. The yield was 98%.

Synthesis Example 4

Synthesis of di-potassium salt of 4,4'-dihydroxydiphenylsulfone.

To a 500 ml four-necked flask equipped with a stirrer, the thermometer, Dean Stark trap having a condenser, and a 100 ml dropping funnel, 30.0 g (0.12 mol) of 4,4'-dihydroxyphenylsulfone, 200.9 g of 1,3-dimethyl-2-imidazolidinone and 96.7 g of p-xylene were charged and heat ed to 115° C. in a nitrogen atmosphere.

To the mixture was, 50.7 g (0.24 mol) of a 26.1 wt % aqueous potassium hydroxide solution was dropwise added from the dropping funnel over 1.5 hours, while separating a distilled water p-xylene mixture in the Dean Stark trap and returning p-xylene alone to the reaction flask. When the internal temperature reached to 160° C., heating was finished and the reaction mass was cooled. The resulting slurry of 4,4'-dihydroxyphenylsulfone di-potassium salt was filtered, washed with toluene, and dried at 120° C. under 5.33 kPa (40 mmHg) for 8 hours and successively at 160° C. under 5.33 kPa (40 mmHg) for 5 hours to obtain 35.8 g of 4,4'-dihydroxydiphenylsulfone di-potassium salt. The yield was 92%.

Example 1

To a 50 ml flask equipped with a stirrer and condenser, 1.10 g (6.2 mmol) of p-nitrophenol potassium salt and 40 g of acetonitrile were charged, successively 6.34 g (46.6 mmol) of DFI was added, and heat-refluxed at 84° C. for 8 hours in a nitrogen atmosphere. After finishing the reaction, the reaction mass was subjected to GC-MS analysis and formation of p-nitrofluorobenzene was confirmed. The reaction yield was 93.6% by GC analysis.

Example 2

To a 50 ml flask equipped with a stirrer and condenser, 1.10 g (6.2 mmol) of p-nitrophenol potassium salt and 40 g of acetonitrile were charged, successively 0.86 g (6.3 mmol) of DFI was added, and heat-refluxed at 84° C. for 5 hours in a nitrogen atmosphere. After finishing the reaction, the reaction mass was subjected to GC-MS analysis and formation of p-nitrofluorobeznene was confirmed. The reaction yield was 50.8% by GC analysis.

Example 3

To a reaction vessel, 1.54 g (5.00 mmol) of 4,4'-dihydroxybenzophenone di-potassium salt, 4.08 g (30.00 mmol) of DFI and 40 ml of acetonitrile were charged and reacted at 80° C. for 8 hours in a nitrogen atmosphere. After finishing the reaction, the reaction mass was subjected to GC-MS analysis and formed 4,4'-difluorobenzophenone was identified by the parent ion 218 and base peak 123. The reaction yield was 50% by GC-analysis.

Example 4

To a reaction vessel, 0.31 g (1.07 mmol) of 4,4'-dihydroxybenzophenone di-potassium salt, 0.29 g (2.14 mmol) of DFI and 30 ml of nitrobenzene were charged and reacted at 120° C. for 4 hours in a nitrogen atmosphere. After finishing the reaction, the reaction mass was subjected to GC-MS analysis and formed 4,4'-difuorobenzophenone was identified by the parent ion 218 and base peak 123. The reaction yield was 45% by GC-analysis.

Comparative Example 1

To a reaction vessel, 1.07 g (5.00 mmol) of 4,4'-dihydroxybenzophenone, 4.08 g (30.00 mmol) of DFI and 50 ml of acetonitrile were charged and reacted at 84° C. for 4 hours in a nitrogen atmosphere. After finishing the reaction, the reaction mass was subjected to GC-MS analysis and formed 4,4'-difluorobenzophenone was identified by the parent ion 218 and base peak 123. The reaction yield was 20% by GC-analysis.

Example 5

To a reaction vessel, 1.18 g (4.12 mmol) of 4,4'-dihydroxydiphenylsulfone mono-potassium salt, 2.33 g (17.09 mmol) of DFI and 10 ml of acetonitrile were charged and reacted at 84° C. for 16 hours in a nitrogen atmosphere. After finishing the reaction, excess DFI was hydrolyzed with an aqueous NaOH solution and the resulting mixture was made acid by addition of an aqueous hydrochloric acid solution and extracted with ether. The ether solution was subjected to thin layer chromatography and formed 4-fluoro-4'-hydroxydiphenylsulfone was identified by EI-MASS molecular ion peak 252. The reaction yield was 64% by HPLC-analysis.

Example 6

To a reaction vessel, 2.82 g (8.64 mmol) of 4,4'-dihydroxydiphenylsulfone di-potassium salt, 7.01 g (51.49 mmol) of DFI and 20 ml of acetonitrile were charged and reacted at 84° C. for 10 hours in a nitrogen atmosphere. After finishing the reaction, excess DFI was hydrolyzed with an aqueous NaOH solution and the resulting mixture was made acid by addition of an aqueous hydrochloric acid solution and extracted with ether. The ether solution was subjected to thin layer chromatography and formed 4,4'-difluorodiphenylsulfone was identified by EI-MASS molecular ion peak 254. The reaction yield was 44% by HPLC-analysis.

Example 7

To a reaction vessel, 19.75 g (145.07 mmol) of DFI and 30 ml of acetonitrile were charged and heated at 84° C. in a nitrogen atmosphere.

Successively, a slurry solution consisting of 4.9g (15.04 mmol) of 4,4'-dihydroxydiphenylsulfone di-potassium salt and 60 ml of acetonitrile was dropwise added over 9 hours and further reacted for 5 hours at the same temperature. The reaction yield of 4,4'-difluorodiphenylsulfone was 70% by HPLC analysis.

Comparative Example 2

To a reaction vessel, 1.08 g (4.32 mmol) of 4,4'-dihydroxydiphenylsulfone, 1.28 g (9.38 mmol) of DFI and 10 ml of acetonitrile were charged and reacted at 84° C. for 6 hours in a nitrogen atmosphere. The reaction yield of 4,4'-difluorodiphenylsulfone was 7% by HPLC analysis.

What is claimed is:

1. A preparation process comprising reacting a compound represented by the formula (1)

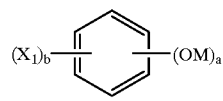

(1)

wherein M is an alkali metal or alkaline earth metal atom, a and b are an integer of 1 to 5 and can be the same or different and a+b is 6 or less, and $X_1$ is a mono-valent group selected from the group consisting of a halogen atom, an alkyl, alkoxy, aryl, aryloxy, nitro, cyano, acyl, per-halogenated alkyl and per-halogenated alkoxy, with an organic fluorinating agent represented by the formula (5-1);

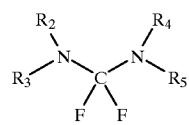

(5-1)

wherein $R_2$, $R_3$, $R_4$ and $R_5$ are an alkyl or aryl group having 1 to 6 carbon atoms and can be the same or different, $R_2$ and $R_3$ or $R_4$ and $R_6$ can bond to form a ring having a nitrogen atom or a nitrogen atom and other hereto atom, $R_2$ and $R_4$ can bond to form a ring having a nitrogen atom or a nitrogen atom and other hereto atoms, to prepare a fluorine substituted aromatic compound represented by the formula (4);

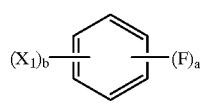

(4)

wherein a, b, and $X_1$ are the same as the above formula (1).

2. A preparation process according to claim 1 wherein the organic fluorinating agent is 2,2'-difluoro-1,3-dimethylimidazolidine represented by the formula (5-2);

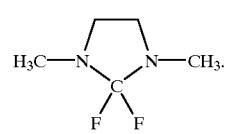

(5-2)

* * * * *

UNITED STATES PATENT AND TRADEMARK OFFICE
CERTIFICATE OF CORRECTION

PATENT NO. : 6,242,654 B1
DATED : June 5, 2001
INVENTOR(S) : Kenichi Goto et al.

Page 1 of 1

It is certified that error appears in the above-identified patent and that said Letters Patent is hereby corrected as shown below:

<u>Title page,</u>
Item [56], under U.S. PATENT DOCUMENTS, change the date of 3,976,691 from "8/1976" to -- 4/1976 --.

<u>Column 24,</u>
Line 34, change "$R_6$" to -- $R_5$ --.

Signed and Sealed this

Second Day of April, 2002

*Attest:*

*Attesting Officer*

JAMES E. ROGAN
*Director of the United States Patent and Trademark Office*